United States Patent
Kimura et al.

(10) Patent No.: US 12,285,732 B2
(45) Date of Patent: *Apr. 29, 2025

(54) UNSATURATED HYDROCARBON PRODUCTION APPARATUS

(71) Applicant: IHI CORPORATION, Tokyo (JP)

(72) Inventors: Hiroyuki Kimura, Tokyo (JP); Satoshi Seo, Tokyo (JP); Shinsuke Matsuno, Tokyo (JP); Tomoya Muramoto, Tokyo (JP)

(73) Assignee: IHI CORPORATION, Tokyo (JP)

(*) Notice: Subject to any disclaimer, the term of this patent is extended or adjusted under 35 U.S.C. 154(b) by 840 days.

This patent is subject to a terminal disclaimer.

(21) Appl. No.: 17/108,456

(22) Filed: Dec. 1, 2020

(65) Prior Publication Data
US 2021/0080176 A1    Mar. 18, 2021

Related U.S. Application Data

(63) Continuation of application No. PCT/JP2019/006331, filed on Feb. 20, 2019.

(30) Foreign Application Priority Data

Jun. 5, 2018 (JP) .................................. 2018-107491
Jun. 29, 2018 (JP) .................................. 2018-124111

(51) Int. Cl.
*B01J 19/12* (2006.01)
*B01J 7/00* (2006.01)

(52) U.S. Cl.
CPC ................ *B01J 19/127* (2013.01); *B01J 7/00* (2013.01); *B01J 2219/0871* (2013.01); *B01J 2219/0892* (2013.01); *F25J 2210/12* (2013.01)

(58) Field of Classification Search
CPC .............. B01J 19/127; B01J 2219/0892; B01J 2208/00451; B01J 2208/00513;
(Continued)

(56) References Cited

U.S. PATENT DOCUMENTS 5,997,837 A     12/1999  Lynum et al.
2002/0090330 A1  7/2002  Smalley et al.
(Continued)

FOREIGN PATENT DOCUMENTS

EP    1341604 A1    9/2003
JP    2005-515295 A  5/2005
(Continued)

OTHER PUBLICATIONS

International Search Report issued in Application No. PCT/JP2019/006331 dated May 7, 2019, 4 pages.
(Continued)

*Primary Examiner* — Imran Akram
(74) *Attorney, Agent, or Firm* — Rothwell, Figg, Ernst & Manbeck, P.C.

(57) ABSTRACT

An unsaturated hydrocarbon production apparatus includes: a light collecting device configured to collect sunlight, and to convert the sunlight into solar heat; and a heating furnace configured to heat a raw material gas containing at least any one selected from the group consisting of methane and hydrogen, methane and oxygen, and ethane with the solar heat generated by the light collecting device to 700° C. or more and 2,000° C. or less.

8 Claims, 3 Drawing Sheets

(58) Field of Classification Search
CPC .. B01J 19/24; B01J 8/087; B01J 8/062; F24S 20/20

See application file for complete search history.

(56) References Cited

U.S. PATENT DOCUMENTS

| | | | |
|---|---|---|---|
| 2003/0208959 A1* | 11/2003 | Weimer | C01B 3/24 |
| | | | 48/197 R |
| 2005/0148806 A1 | 7/2005 | Cruijsberg et al. | |
| 2006/0205989 A1 | 9/2006 | Little et al. | |
| 2008/0156630 A1 | 7/2008 | Lee et al. | |
| 2010/0305221 A1 | 12/2010 | Schunk et al. | |
| 2010/0314235 A1 | 12/2010 | Varadaraj et al. | |
| 2011/0226988 A1 | 9/2011 | McAlister | |
| 2012/0219490 A1 | 8/2012 | Noda et al. | |
| 2012/0241677 A1 | 9/2012 | Perkins et al. | |
| 2013/0025192 A1* | 1/2013 | Wegeng | H01M 8/0612 |
| | | | 44/457 |
| 2014/0086820 A1 | 3/2014 | Nakamura et al. | |
| 2014/0179810 A1* | 6/2014 | Yoon | B01J 19/127 |
| | | | 518/711 |
| 2016/0121295 A1* | 5/2016 | Chen | F24S 23/77 |
| | | | 422/108 |
| 2016/0362351 A1 | 12/2016 | Nagaki et al. | |
| 2021/0080176 A1 | 3/2021 | Kimura et al. | |
| 2021/0086157 A1 | 3/2021 | Kimura et al. | |
| 2021/0147228 A1* | 5/2021 | Geerlings | C01B 32/16 |

FOREIGN PATENT DOCUMENTS

| | | |
|---|---|---|
| JP | 2006-522081 A | 9/2006 |
| JP | 2008-303184 A | 12/2008 |
| JP | 2008-545603 A | 12/2008 |
| JP | 2010-526759 A | 8/2010 |
| JP | 2015-196619 A | 11/2015 |
| JP | 2016-055209 A | 4/2016 |
| JP | 2017-178827 A | 10/2017 |
| WO | 03/049853 A1 | 6/2003 |
| WO | 2019/197253 A1 | 10/2019 |
| WO | 2019/234992 A1 | 12/2019 |
| WO | WO2019/234991 A1 | 6/2021 |

OTHER PUBLICATIONS

J. Yeheskel, et al., "Thermolysis of methane in a solar reactor for mass-production of hydrogen and carbon nano-materials", Carbon 49 (2011) pp. 4695-4703.

N.M. Mubarak, et al., "An overview on methods for the production of carbon nanotubes", Journal of Industrial and Engineering Chemistry 20 (2014) pp. 1186-1197.

K. A. Shah, et al., "Synthesis of carbon nanotubes by catalytic chemical vapour deposition: A review on carbon sources, catalysts and substrates", Materials Science in Semiconductor Processing 41 (2016) pp. 67-82.

E. Diaz, et al., "New concentrated solar power plants based on fuel cells", 9th International Exergy, Energy and Environment Symposium (IEEES-9), May 14-17, 2017, Split, Croatia, pp. 1-12.

A. Holmen, "Direct conversion of methane to fuels and chemicals", Catalysis Today 142 (2009) pp. 2-8.

Homichenko V.I., et al., "CH4/H2 ratio effect on methane pyrolysis on resistive molybdenum catalyst", Procedia Engineering 113 (2015) pp. 138-143.

The extended European search report mailed Mar. 23, 2022 in corresponding EP Patent Application No. 19815257.1 (10 pages).

C. Agrafiotis et al., "Solar thermal reforming of methane feedstocks for hydrogen and syngas production—A review", Renewable and Sustainable Energy Reviews, vol. 29, 2014, pp. 656-682.

S. Abanades et al., "Production of hydrogen by thermal methane splitting in a nozzle-type laboratory-scale solar reactor", International Journal of Hydrogen Energy, vol. 30, No. 8, 2005, pp. 843-853.

The extended European search report mailed Feb. 14, 2022 in corresponding EP Patent Application No. 19814930.4 (9 pages).

* cited by examiner

UNSATURATED HYDROCARBON PRODUCTION APPARATUS

CROSS REFERENCE TO RELATED APPLICATIONS

This application is a continuation application of International Application No. PCT/JP2019/006331, filed on Feb. 20, 2019, which claims priority to Japanese Patent Application No. 2018-107491 filed on Jun. 5, 2018 and Japanese Patent Application No. 2018-124111 filed on Jun. 29, 2018, the entire contents of which are incorporated by reference herein.

BACKGROUND ART

Technical Field

The present disclosure relates to an unsaturated hydrocarbon production apparatus.

Related Art

Ethylene or acetylene serves as a raw material for plastic. Ethylene or acetylene is generated by heating a raw material such as kerosene, naphtha, propane, or ethane to about 900° C., followed by pyrolysis.

The raw material has hitherto been heated by combusting fossil fuel, such as petroleum, with a burner (for example, Patent Literature 1).

CITATION LIST

Patent Literature

Patent Literature 1: JP 2017-178827 A

SUMMARY

Technical Problem

However, in the related art, an exhaust gas containing carbon dioxide ($CO_2$), sulfur oxides ($SO_x$), and nitrogen oxides ($NO_x$) is emitted along with the combustion of fossil fuel. Carbon dioxide contained in the exhaust gas is regarded as one of greenhouse gases that are considered to cause global warming. Therefore, there is a demand for the development of a technology of pyrolyzing a raw material while reducing the emission amount of carbon dioxide.

In view of the above-mentioned problem, the present disclosure has an object to provide an unsaturated hydrocarbon production apparatus capable of reducing the emission amount of carbon dioxide.

Solution to Problem

In order to solve the above-mentioned problem, according to one aspect of the present disclosure, there is provided an unsaturated hydrocarbon production apparatus, including: a light collecting device configured to collect sunlight, and to convert the sunlight into solar heat; and a heating furnace configured to heat a raw material gas containing at least any one selected from the group consisting of methane and hydrogen, methane and oxygen, and ethane with the solar heat generated by the light collecting device to 700° C. or more and 2,000° C. or less.

In addition, the unsaturated hydrocarbon production apparatus may further include a cooling unit configured to rapidly cool a generated gas generated in the heating furnace to 600° C. or less.

In addition, the heating furnace may accommodate a catalyst for accelerating a reaction of the raw material gas to any one or both of ethylene and acetylene.

In addition, the unsaturated hydrocarbon production apparatus may further include a preheating unit configured to preheat the raw material gas with heat released from the heating furnace.

In addition, the unsaturated hydrocarbon production apparatus may further include a first heat exchange unit configured to subject the generated gas generated in the heating furnace and the raw material gas to heat exchange, wherein the raw material gas subjected to heat exchange in the first heat exchange unit is introduced into the preheating unit.

In addition, the unsaturated hydrocarbon production apparatus may further include a second heat exchange unit configured to subject the generated gas generated in the heating furnace and the raw material gas preheated by the preheating unit to heat exchange.

In addition, the unsaturated hydrocarbon production apparatus may further include a separation unit configured to separate ethylene or acetylene from a generated gas generated in the heating furnace.

In addition, the heating furnace may be configured to heat the raw material gas to 1,000° C. or more and 1,200° C. or less.

Effects of Disclosure

According to the present disclosure, the emission amount of carbon dioxide can be reduced.

DESCRIPTION OF EMBODIMENTS

Figure 1:
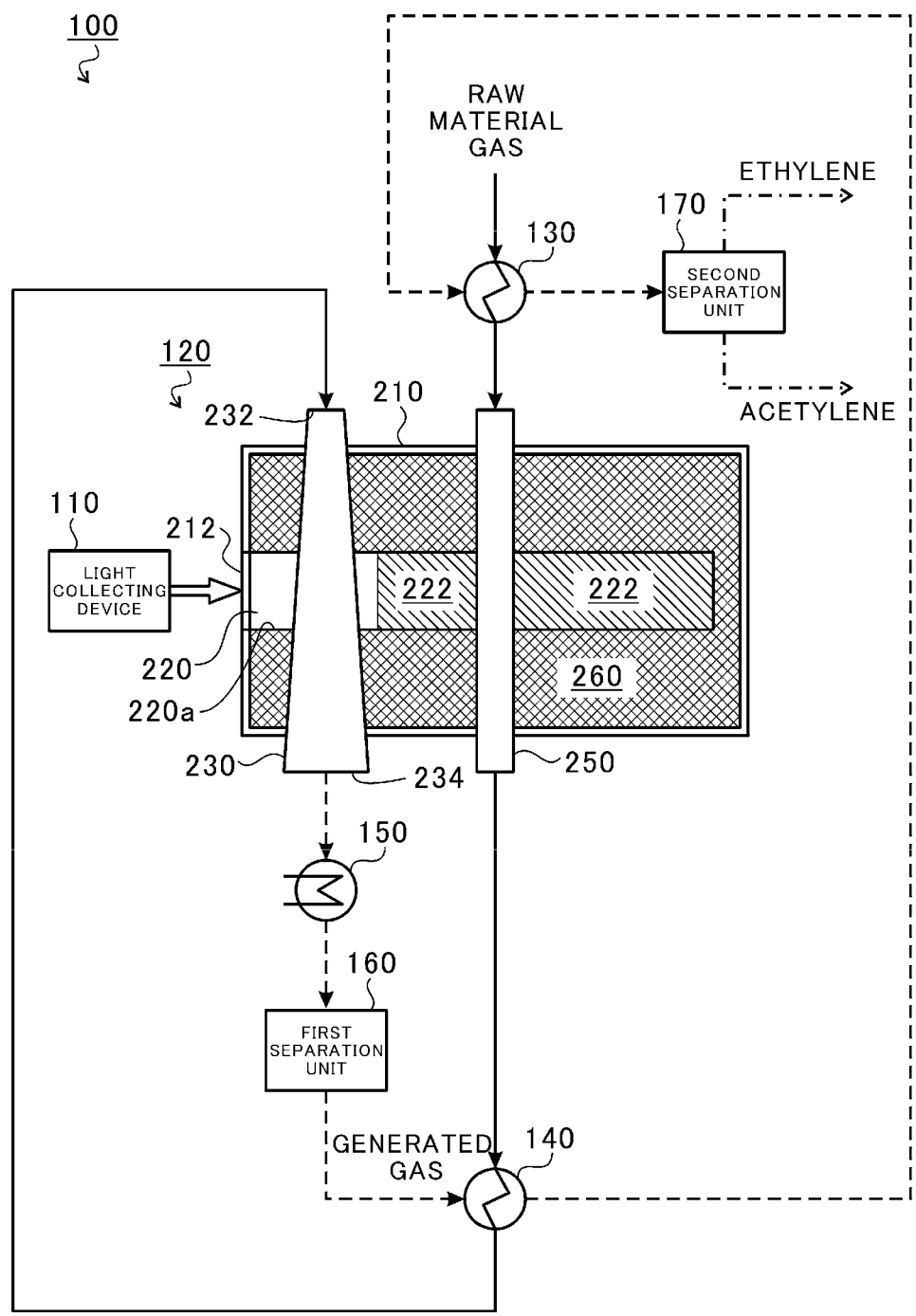
FIG. 1 is a diagram for illustrating an unsaturated hydrocarbon production apparatus according to a first embodiment.

Now, with reference to the attached drawings, embodiments of the present disclosure are described in detail. Dimensions, materials, and other specific numerical values represented in the embodiments are merely examples used for facilitating the understanding of the disclosure, and do not limit the present disclosure otherwise particularly noted. Elements having substantially the same functions and configurations herein and in the drawings are denoted by the same reference symbols to omit redundant description thereof. In addition, illustration of elements with no direct relationship to the present disclosure is omitted.

First Embodiment

FIG. 1 is a diagram for illustrating an unsaturated hydrocarbon production apparatus 100 according to a first embodiment. In FIG. 1, the solid line arrows each indicate a flow of a raw material gas. In FIG. 1, the broken line arrows each indicate a flow of a generated gas. In addition, in FIG. 1, the alternate long and short dash line arrows each indicate a flow of ethylene or acetylene. In FIG. 1, the outlined arrow indicates collected sunlight.

As illustrated in FIG. 1, the unsaturated hydrocarbon production apparatus 100 includes a light collecting device 110, a heating unit 120, a first heat exchange unit 130, a second heat exchange unit 140, a cooling unit 150, a first separation unit 160, and a second separation unit 170 (separation unit).

The light collecting device 110 is configured to collect sunlight, and to guide the sunlight to the heating unit 120 (lighting window 212). The heating unit 120 includes a housing 210, a furnace chamber 220, a heat transfer material 222, a heating furnace 230, a preheating unit 250, and a heat insulating material 260. In FIG. 1, the heat transfer material 222 is indicated by hatching, and the heat insulating material 260 is indicated by cross hatching.

Figure 2A:
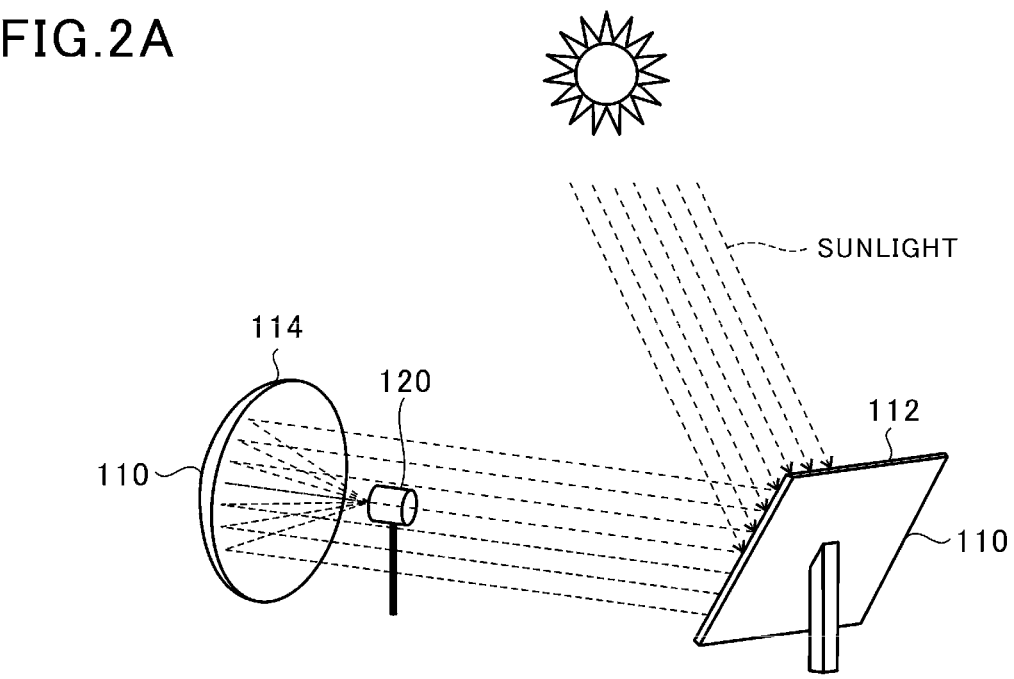
FIG. 2A is a view for illustrating an external appearance of each of a light collecting device and a heating unit.
Figure 2B:
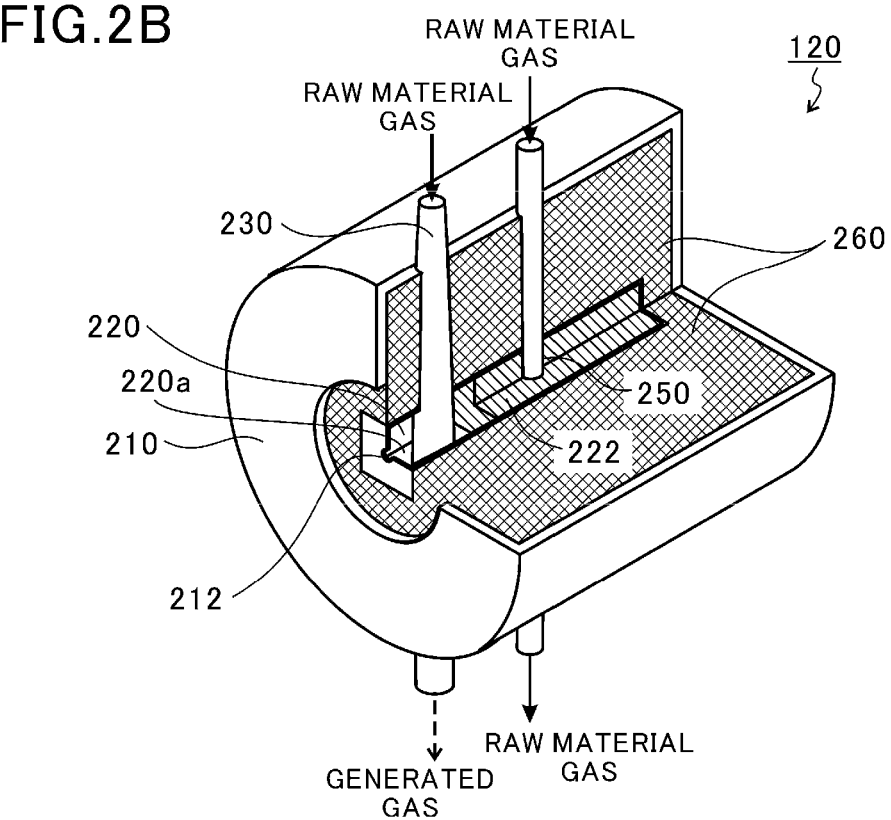
FIG. 2B is a partially cutaway perspective view of the heating unit.

FIG. 2A is a view for illustrating an external appearance of each of the light collecting device 110 and the heating unit 120. FIG. 2B is a partially cutaway perspective view of the heating unit 120. In FIG. 2B, the heat transfer material 222 is indicated by hatching, and the heat insulating material 260 is indicated by cross hatching.

As illustrated in FIG. 2A, the light collecting device 110 is a device configured to collect the sunlight, and to convert the sunlight into solar heat. The light collecting device 110 includes one or a plurality of heliostats (plane mirrors) 112, a parabolic curved mirror 114, and a furnace wall 220a described later. The heliostat 112 is configured to reflect and guide the sunlight to the parabolic curved mirror 114. The parabolic curved mirror 114 is a mirror having a reflecting surface in a concave shape. The parabolic curved mirror 114 is configured to collect the sunlight reflected by the heliostat 112, and to guide the sunlight to the heating unit 120 (lighting window 212).

As illustrated in FIG. 2B, the housing 210 of the heating unit 120 has a cylindrical shape. The housing 210 is provided so that the axial direction thereof is matched with a horizontal direction. The lighting window 212 is formed on a side surface of the housing 210. The furnace chamber 220 is formed in the housing 210 so as to be contiguous to the lighting window 212. That is, the lighting window 212 partitions the furnace chamber 220 from an outside. The furnace chamber 220 is a space extending in the horizontal direction. The furnace wall 220a forming the furnace chamber 220 is made of an endothermic material (inorganic material having high heat resistance, such as black ceramics).

The heating furnace 230 and the preheating unit 250 each have a tube shape. The heating furnace 230 and the preheating unit 250 are provided so as to penetrate through the furnace chamber 220. The heating furnace 230 is provided at a position closest to the lighting window 212. The preheating unit 250 is adjacent to the heating furnace 230. That is, the heating furnace 230 and the preheating unit 250 are provided in the furnace chamber 220 in the stated order from the side closer to the lighting window 212. In the furnace chamber 220, the heat transfer material 222 is arranged between the heating furnace 230 and the preheating unit 250 and between the preheating unit 250 and the heat insulating material 260. That is, the heat transfer material 222 is separated from the heating furnace 230, and surrounds the preheating unit 250. The heat transfer material 222 is, for example, graphite or ceramics.

The sunlight that has passed through the lighting window 212 and guided to an inside of the furnace chamber 220 is, for example, radiated to the heating furnace 230 or radiated to the furnace wall 220a forming the furnace chamber 220, thereby being converted into thermal energy (solar heat) to heat the heating furnace 230 and the furnace wall 220a. With this, the heating furnace 230 is maintained at 1,000° C. or more and 2,000° C. or less. The heat transfer material 222 is not in contact with the heating furnace 230, with the result that the entire circumference of the heating furnace 230 is exposed to radiation. With this, the heating furnace 230 is efficiently heated with the sunlight. In addition, the heat (heat radiation) released from the heating furnace 230 is transmitted to the preheating unit 250 through the heat transfer material 222, and the preheating unit 250 is maintained at a predetermined preheating temperature (temperature exceeding normal temperature (25° C.)). When the heat transfer material 222 comes into contact with the entire circumference of the preheating unit 250, the preheating unit 250 is efficiently heated.

The heat insulating material 260 is arranged in the housing 210. The heat insulating material 260 surrounds the furnace chamber 220. The heat insulating material 260 suppresses the outflow of heat (heat radiation) from the furnace chamber 220 to the outside.

Returning to the description with reference to FIG. 1, the first heat exchange unit 130 is configured to subject a generated gas (described later in detail), which is generated in the heating furnace 230 and has heat removed therefrom by the second heat exchange unit 140 described later, and a raw material gas to heat exchange. With this, the raw material gas is heated with the heat of the generated gas, and the generated gas is cooled. The raw material gas is a gas containing at least methane and hydrogen. The raw material gas is, for example, a mixed gas of a natural gas and hydrogen. The raw material gas heated by the first heat exchange unit 130 is sent to the preheating unit 250. Meanwhile, the generated gas cooled by the first heat exchange unit 130 is sent to a second separation unit 170 described later.

As described above, the preheating unit 250 is maintained at the preheating temperature with the heat radiation from the heating furnace 230. Therefore, the preheating unit 250 can preheat (heat) the raw material gas heated by the first heat exchange unit 130 to the preheating temperature.

The second heat exchange unit 140 is configured to subject the raw material gas preheated by the preheating unit 250 and the generated gas discharged from the heating furnace 230 to heat exchange. With this, the raw material gas is heated with the heat of the generated gas, and the generated gas is cooled. The raw material gas heated by the second heat exchange unit 140 is introduced into the heating furnace 230. Meanwhile, the generated gas cooled by the second heat exchange unit 140 is introduced into the first heat exchange unit 130.

The raw material gas heated by the first heat exchange unit 130, the preheating unit 250, and the second heat exchange unit 140 is introduced into the heating furnace 230.

The raw material gas introduced into the heating furnace 230 is maintained at 1,000° C. or more and 2,000° C. or less by the light collecting device 110 as described above. Then, for example, reactions represented by the following reaction formula (1) and reaction formula (2) proceed, and methane ($CH_4$) contained in the raw material gas is converted into ethylene ($C_2H_4$) and acetylene ($C_2H_2$).

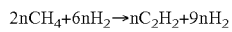   Reaction Formula (1)

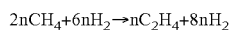   Reaction Formula (2)

In the reaction formulae including the reaction formula (1) and the reaction formula (2), "n" represents an integer of 1 or more.

The amount of hydrogen in the raw material gas introduced into the heating furnace 230 is 0.1 mol or more and 8 mol or less with respect to methane (1 mol) in the raw material gas. The amount of hydrogen in the raw material gas is preferably 3 mol or more with respect to methane in the raw material gas. When hydrogen is introduced in an amount of 3 mol or more with respect to methane, the heating furnace 230 can improve the yield of ethylene and acetylene.

Hydrogen has a relatively large heat capacity. Therefore, when hydrogen is introduced in an amount of more than 8 mol with respect to methane, the thermal energy required for maintaining the temperature of the heating furnace 230 is increased. In view of the foregoing, hydrogen is introduced into the heating furnace 230 in an amount of 8 mol or less with respect to methane. With this, the thermal energy supplied in order to maintain the temperature of the heating furnace 230 at 1,000° C. or more and 2,000° C. or less can be reduced.

In addition, when the yield of ethylene is improved as compared to acetylene, it is appropriate that the light collecting device 110 heat the raw material gas in the heating furnace 230 to 1,000° C. or more and 1,200° C. or less. Meanwhile, when the yield of acetylene is improved as compared to ethylene, it is appropriate that the light collecting device 110 heat the raw material gas in the heating furnace 230 to 1,200° C. or more and 1,600° C. or less.

As described above, when the raw material gas is introduced into the heating furnace 230, a generated gas containing at least ethylene, acetylene, and unreacted hydrogen is generated.

The cooling unit 150 is configured to rapidly cool the generated gas generated in the heating furnace 230 to 600° C. or less. With this, the cooling unit 150 can suppress the pyrolysis of ethylene and acetylene contained in the generated gas.

The generated gas rapidly cooled by the cooling unit 150 is introduced into the first separation unit 160. The first separation unit 160 includes a ceramic hydrogen separation membrane (for example, a porous ceramic hydrogen separation membrane). The first separation unit 160 is configured to separate and remove hydrogen from the generated gas. With the configuration including the first separation unit 160, the unsaturated hydrocarbon production apparatus 100 can reduce the amount of hydrogen in the generated gas. The generated gas having hydrogen removed therefrom by the first separation unit 160 is subjected to heat exchange by the above-mentioned second heat exchange unit 140 and first heat exchange unit 130, and then is introduced into the second separation unit 170.

The second separation unit 170 includes, for example, a microporous metal-organic framework material. The second separation unit 170 is configured to separate the generated gas into ethylene and acetylene. With the configuration including the second separation unit 170, the unsaturated hydrocarbon production apparatus 100 can increase the purity of acetylene as well as the purity of ethylene. Then, the ethylene separated by the second separation unit 170 is sent to a facility in a subsequent stage (for example, a plastic (resin) production plant). In addition, the acetylene separated by the second separation unit 170 is sent to a facility in a subsequent stage (for example, a fuel production plant).

As described above, in the unsaturated hydrocarbon production apparatus 100 according to the first embodiment, the light collecting device 110 is configured to heat the raw material gas in the heating furnace 230. With this, the unsaturated hydrocarbon production apparatus 100 can reduce the emission amount of carbon dioxide to substantially 0 (zero) when generating ethylene and acetylene (unsaturated hydrocarbons). That is, the unsaturated hydrocarbon production apparatus 100 does not newly generate carbon dioxide in a process of obtaining a heating source, unlike the case of using the combustion heat of fossil resources or the electric energy derived therefrom in order to obtain a heating source. Therefore, the unsaturated hydrocarbon production apparatus 100 can improve the effect of reducing carbon dioxide. Further, the unsaturated hydrocarbon production apparatus 100 is not required to consume valuable fossil resources in order to obtain a heating source, with the result that the cost required for heating can be significantly suppressed.

Solid carbon may be generated in the heating furnace 230 depending on the content of hydrogen in the raw material gas. In this case, as illustrated in FIG. 1, the shape of the heating furnace 230 is designed so that the diameter of an upper opening 232 is smaller than the diameter of a lower opening 234, and a flow passage sectional area (horizontal sectional area) is gradually increased from the upper opening 232 to the lower opening 234. In addition, the heating furnace 230 is made of a material having a linear expansion coefficient different from that of the solid carbon. The heating furnace 230 is made of a ceramic material, such as alumina, stearite, forsterite, or zirconia.

With this, in the unsaturated hydrocarbon production apparatus 100, a difference can be made between the thermal expansion amount of the heating furnace 230 and the thermal expansion amount of the solid carbon adhering to an inner wall of the heating furnace 230 by changing the temperature in the heating furnace 230 during a period of time in which the production of unsaturated hydrocarbons (ethylene and acetylene) is suspended. Thus, even when the solid carbon has adhered to the inner wall of the heating furnace 230, the unsaturated hydrocarbon production apparatus 100 can apply a shearing force along a contact surface between the heating furnace 230 and the solid carbon by making a difference between those thermal expansion amounts.

That is, the unsaturated hydrocarbon production apparatus 100 can reduce the adhesion force between the inner wall of the heating furnace 230 and the solid carbon, and can induce peeling of the solid carbon from the inner wall of the heating furnace 230. The peeled solid carbon falls outside the heating furnace 230 by the own weight thereof through the lower opening 234.

In addition, as described above, the unsaturated hydrocarbon production apparatus 100 includes the first heat exchange unit 130. With this, the first heat exchange unit 130 can heat the raw material gas with the heat of the generated gas. Further, the unsaturated hydrocarbon production apparatus 100 includes the preheating unit 250. With this, the preheating unit 250 can preheat the raw material gas with the heat released from the heating furnace 230. In addition, the unsaturated hydrocarbon production apparatus 100 includes the second heat exchange unit 140. With this, the second heat exchange unit 140 can heat the raw material gas with the heat of the generated gas. As described above, the unsaturated hydrocarbon production apparatus 100 can heat the raw material gas with exhaust heat, and hence the cost required for heating can be suppressed.

Second Embodiment

The heating furnace 230 according to the above-mentioned first embodiment does not accommodate a catalyst. However, a heating furnace 330 may accommodate the catalyst.

Figure 3:
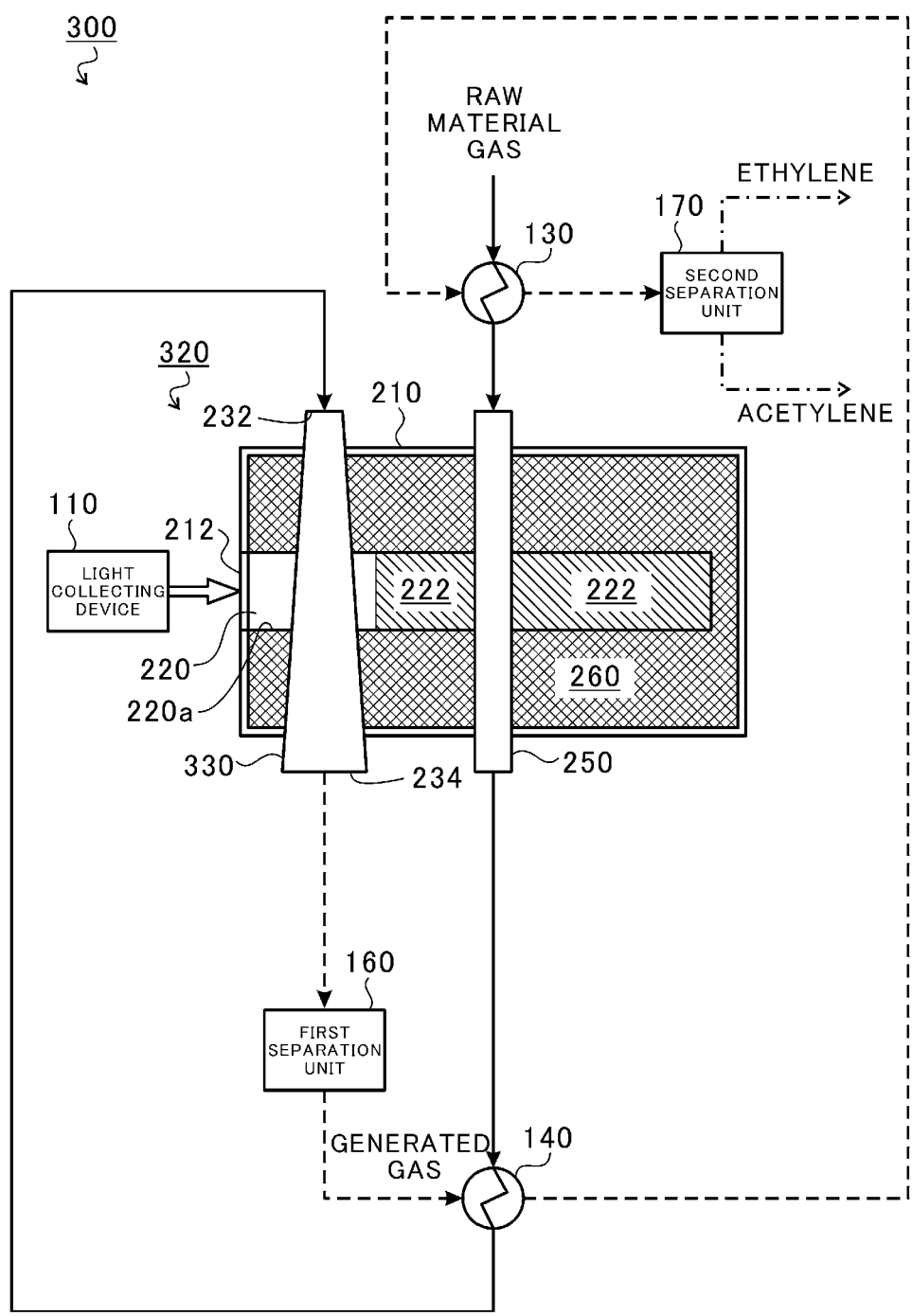
FIG. 3 is a diagram for illustrating an unsaturated hydrocarbon production apparatus according to a second embodiment.

FIG. 3 is a diagram for illustrating an unsaturated hydrocarbon production apparatus 300 according to a second embodiment. In FIG. 3, the solid line arrows each indicate a flow of the raw material gas. In FIG. 3, the broken line arrows each indicate a flow of the generated gas. In FIG. 3, the alternate long and short dash line arrows each indicate a flow of ethylene or acetylene. In FIG. 3, the outlined arrow indicates collected sunlight.

As illustrated in FIG. 3, the unsaturated hydrocarbon production apparatus 300 includes the light collecting device 110, a heating unit 320, the first heat exchange unit 130, the second heat exchange unit 140, the first separation unit 160, and the second separation unit 170. In addition, the heating unit 320 includes the housing 210, the furnace chamber 220, the heat transfer material 222, the heating furnace 330, the preheating unit 250, and the heat insulating material 260. Constituent elements that are substantially equal to those of the above-mentioned unsaturated hydrocarbon production apparatus 100 are denoted by the same reference symbols as those therein, and description thereof is omitted. In addition, in FIG. 3, the heat transfer material 222 is indicated by hatching, and the heat insulating material 260 is indicated by cross hatching.

The heating furnace 330 accommodates a catalyst for accelerating the reaction of the raw material gas to any one or both of ethylene and acetylene (for example, the reaction represented by the above-mentioned reaction formula (1) or the reaction represented by the above-mentioned reaction formula (2)). The heating furnace 330 accommodates a catalyst as a packed bed. Examples of the catalyst for accelerating the reaction of the raw material gas to any one or both of ethylene and acetylene include one or a plurality of catalysts selected from the group consisting of molybdenum (Mo), tungsten (W), iron (Fe), vanadium (V), and chromium (Cr).

When the heating furnace 330 accommodates the catalyst, the pyrolysis of ethylene and acetylene can be suppressed without rapidly cooling the generated gas. With this, as compared to the unsaturated hydrocarbon production apparatus 100, the unsaturated hydrocarbon production apparatus 300 can omit the cooling unit 150. Therefore, the unsaturated hydrocarbon production apparatus 300 can improve the heat recovery efficiency of the generated gas by the second heat exchange unit 140.

In addition, when the heating furnace 330 accommodates the catalyst, the amount of hydrogen in the raw material gas is preferably 0.5 mol or more, more preferably 1 mol or more, still more preferably 1.5 mol or more with respect to methane in the raw material gas. When hydrogen is introduced in an amount of 0.5 mol or more with respect to methane, the yield of ethylene and acetylene can be improved.

The embodiments have been described above with reference to the attached drawings, but, needless to say, the present disclosure is not limited to the embodiments. It is apparent that those skilled in the art may arrive at various alternations and modifications within the scope of claims, and those examples are construed as naturally falling within the technical scope of the present disclosure.

For example, in the above-mentioned embodiments, the description has been given of the example of the case in which the raw material gas is a gas containing at least methane and hydrogen. However, the raw material gas may be a gas containing at least methane and oxygen. In this case, the light collecting device 110 may heat the raw material gas in the heating furnace 330 to 700° C. or more and 2,000° C. or less. Then, for example, the oxidative coupling reaction represented by the following reaction formula (3) proceeds, and methane contained in the raw material gas is converted into ethylene.

$2nCH_4+nO_2 \rightarrow nC_2H_4+2nH_2O$  Reaction Formula (3)

In addition, in this case, the heating furnace 330 accommodates a catalyst for accelerating the oxidative coupling reaction represented by the above-mentioned reaction formula (3). Examples of the catalyst for accelerating the oxidative coupling reaction include one or a plurality of catalysts selected from the group consisting of $SrO/La_2O_3$, $Mn/Na_2WO_4/SiO_2$, $Li/MgO$, $Ba\ F_2/Y_2O_3$, $Rb_2WO_4/SiO_2$, $La_2O_3-CeO_2$, and $Na_2WO_4/SiO_2$.

Further, when the raw material gas is a gas containing at least methane and oxygen, methane in the raw material gas may be partially oxidized to cause the reaction represented by the following reaction formula (4) to proceed, to thereby convert methane into acetylene.

$2nCH_4+nO_2 - nC_2H_2+nH_2+2nH_2O$  Reaction Formula (4)

In this case, the light collecting device 110 may heat the raw material gas in the heating furnace 230 to about 1,500° C.

In addition, the raw material gas may be a gas containing at least ethane ($C_2H_6$). In this case, the light collecting device 110 may heat the raw material gas in each of the heating furnaces 230 and 330 to 1,000° C. or more and 2,000° C. or less. Then, for example, a pyrolysis (cracking) reaction represented by the following reaction formula (5) proceeds, and ethane contained in the raw material gas is converted into ethylene.

$nC_2H_6 \rightarrow nC_2H_4+nH_2$  Reaction Formula (5)

Further, the raw material gas may be a gas containing at least ethane and hydrogen. In this case, the light collecting device 110 may heat the raw material gas in each of the heating furnaces 230 and 330 to 1,000° C. or more and 2,000° C. or less. Then, for example, pyrolysis (cracking) reactions represented by the following reaction formula (6) and reaction formula (7) proceed, and ethane contained in the raw material gas is converted into ethylene and acetylene.

$nC_2H_6+3nH_2 \rightarrow nC_2H_2+5nH_2$  Reaction Formula (6)

$nC_2H_6+3nH_2 \rightarrow nC_2H_4+4nH_2$  Reaction Formula (7)

In addition, the raw material gas may be a gas containing at least ethane and oxygen. In this case, ethane in the raw material gas may be partially oxidized to cause the reaction represented by the following reaction formula (8) to proceed, to thereby convert ethane into acetylene.

$nC_2H_6+nO_2 \rightarrow nC_2H_2+2nH_2O$  Reaction Formula (8)

In this case, the light collecting device 110 may heat the raw material gas in the heating furnace 230 to about 1,500° C.

In addition, in the above-mentioned embodiments, the description has been given of the example of the case in which each of the heating furnaces 230 and 330 has such a shape that the flow passage sectional area is gradually increased from the upper opening 232 to the lower opening 234. However, in each of the heating furnaces 230 and 330, the flow passage sectional area in a portion located in the furnace chamber 220 may be smaller than the other flow passage sectional areas. With this, the heating furnaces 230 and 330 can each shorten the residence time period of the raw material gas under a temperature environment of 700° C. or more and 2,000° C. or less. That is, when the residence time period is shortened, and the flow velocity is increased, a laminar convection heat transfer condition is switched to a turbulent convection heat transfer condition, and the heat transfer rate from the heating furnaces 230 and 330 to the raw material gas can increased (the raw material gas can be rapidly heated). In addition, the residence time period is shortened, that is, the heating time is shortened, and hence the time from heating of the raw material gas to cooling thereof is shortened (the raw material gas can be rapidly cooled). In other words, when the heating furnaces 230 and 330 are each designed so that the flow passage sectional area of the portion located in the furnace chamber 220 is smaller than the other flow passage sectional areas, the raw material gas can be rapidly cooled immediately after being rapidly heated. With this, the progress of the pyrolysis of ethylene and acetylene contained in the generated gas generated by rapid heating can be suppressed. Therefore, the yield of ethylene and acetylene in the generated gas can be increased. It is appropriate that, in each of the heating chambers 230 and 330, inert particles be filled into the portion located in the furnace chamber 220 to narrow the flow passage sectional area. In this case, the inert particles that are brought into contact with the inner wall of each of the heating furnaces 230 and 330 are heated by heat conduction from the inner wall of each of the heating furnaces 230 and 330. Therefore, the raw material gas is heated from the surface of each of the inert particles in addition to the surface of the inner wall of each of the heating furnaces 230 and 330 (that is, the heat transfer area is increased). With this, the heating furnaces 230 and 330 can further rapidly heat the raw material gas.

In addition, in the above-mentioned embodiments, the description has been given of the example of the case in which the housing 210 of each of the heating units 120 and 320 has a cylindrical shape. However, the shape of the housing 210 of each of the heating units 120 and 320 is not limited. Further, in the above-mentioned embodiments, the description has been given of the example of the case in which the housing 210 is provided so that the axial direction thereof is matched with the horizontal direction. However, the setting direction of the housing 210 is not limited. For example, the housing 210 may be provided so that the axial direction thereof is matched with a direction crossing the horizontal direction.

In addition, in the above-mentioned embodiments, the description has been given of the example of the heating units 120 and 320 of an indirect heating type in which each of the heating furnaces 230 and 330 is arranged in the furnace chamber 220, and the raw material gas passing through each of the heating furnaces 230 and 330 is indirectly heated. However, the unsaturated hydrocarbon production apparatus 100 and 300 may each include a heating unit of a direct heating type, which includes the lighting window 212 having airtightness, and in which the raw material gas is directly introduced into the furnace chamber 220 to be directly heated.

In addition, in the above-mentioned embodiments, the description has been given of the example of the light collecting device 110 including the heliostat 112 and the parabolic curved mirror 114. However, as long as the light collecting device 110 can collect sunlight and generate solar heat, the kind and configuration thereof are not limited. For example, the light collecting device 110 may be a tower-type light collecting device.

In addition, in the above-mentioned embodiments, the description has been given of the example of the light collecting device 110 serving as a heating source for each of the heating furnaces 230 and 330. However, the heating source for each of the heating furnaces 230 and 330 is not limited to the light collecting device 110. As the heating source for each of the heating furnaces 230 and 330, a combustion device, an electric heater, or the like may be used instead of or in addition to the light collecting device 110. While the function of the light collecting device 110 is decreased, for example, in cloudy weather or rainy weather, the heating source for each of the heating furnaces 230 and 330 may be switched to the combustion device or the electric heater. The combustion device may combust the raw material gas or hydrogen separated by the first separation unit 160.

In addition, in the above-mentioned embodiments, the description has been given of the example of the configuration in which each of the unsaturated hydrocarbon production apparatus 100 and 300 includes the preheating unit 250. However, the preheating unit 250 is not an essentially required configuration.

In addition, in the above-mentioned embodiments, the description has been given of the example of the configuration in which each of the unsaturated hydrocarbon production apparatus 100 and 300 includes the first heat exchange unit 130. However, the first heat exchange unit 130 is not an essentially required configuration.

In addition, in the above-mentioned embodiments, the description has been given of the example of the configuration in which each of the unsaturated hydrocarbon production apparatus 100 and 300 includes the second heat exchange unit 140. However, the second heat exchange unit 140 is not an essentially required configuration.

In addition, in the above-mentioned embodiments, the description has been given of the example of the case in which each of the heating furnaces 230 and 330 and the preheating unit 250 extend in a vertical direction. However, any one or a plurality of each of the heating furnaces 230 and 330 and the preheating unit 250 may extend in a direction crossing the vertical direction (for example, the horizontal direction).

In addition, in the above-mentioned embodiments, the description has been given of the example of the configuration in which the second separation unit 170 includes the microporous metal-organic framework material. However, the configuration of the second separation unit 170 is not limited as long as ethylene or acetylene can be separated from the generated gas. The second separation unit 170 may contain, for example, an absorbent that dissolves acetylene.

In addition, the raw material gas may be preheated with the heat recovered by the cooling unit 150.

In addition, hydrogen separated by the first separation unit 160 may be used as the raw material gas.

INDUSTRIAL APPLICABILITY

The present disclosure is applicable to an unsaturated hydrocarbon production apparatus.

What is claimed is:
1. An unsaturated hydrocarbon production apparatus, comprising:

a light collecting device configured to collect sunlight, and to convert the sunlight into solar heat;

a heating furnace configured to heat a raw material gas containing at least methane and hydrogen with the solar heat generated by the light collecting device to 700° C. or more and 2,000° C. or less; and a source of the raw material gas, wherein an amount of the hydrogen in the raw material gas is 3 mol or more and 8 mol or less per 1 mol of the methane in the raw material gas, the heating furnace includes a tube and a furnace chamber, the tube comprises a first part, a second part, and a third part that is provided between the first part and the second part, the first part is connected to the source of the raw material gas, the second part is connected to a send destination of the generated gas, the first part and the second part are located outside the furnace chamber, the third part is located in the furnace chamber, and the flow passage sectional area in the third part is smaller than the flow passage sectional area in the first part and the second part.

2. The unsaturated hydrocarbon production apparatus according to claim 1, further comprising a cooling unit configured to rapidly cool a generated gas generated in the heating furnace to 600° C. or less.

3. The unsaturated hydrocarbon production apparatus according to claim 1, wherein the heating furnace accommodates a catalyst for accelerating a reaction of the raw material gas to any one or both of ethylene and acetylene.

4. The unsaturated hydrocarbon production apparatus according to claim 1, further comprising a preheating unit configured to preheat the raw material gas with heat released from the heating furnace.

5. The unsaturated hydrocarbon production apparatus according to claim 4, further comprising a first heat exchange unit configured to subject the generated gas generated in the heating furnace and the raw material gas to heat exchange, wherein the raw material gas subjected to heat exchange in the first heat exchange unit is introduced into the preheating unit.

6. The unsaturated hydrocarbon production apparatus according to claim 4, further comprising a second heat exchange unit configured to subject the generated gas generated in the heating furnace and the raw material gas preheated by the preheating unit to heat exchange.

7. The unsaturated hydrocarbon production apparatus according to claim 1, further comprising a separation unit configured to separate ethylene or acetylene from the generated gas generated in the heating furnace.

8. The unsaturated hydrocarbon production apparatus according to claim 1, wherein the heating furnace is configured to heat the raw material gas to 1,000° C. or more and 1,200° C. or less.

* * * * *